(12) United States Patent
Widman et al.

(10) Patent No.: US 10,492,675 B2
(45) Date of Patent: Dec. 3, 2019

(54) SYSTEM AND METHOD FOR DETERMINING CORRECTIVE VISION

(71) Applicant: Johnson & Johnson Vision Care, Inc., Jacksonville, FL (US)

(72) Inventors: Michael F. Widman, Jacksonville, FL (US); James Timothy Davis, Jacksonville, FL (US); Jasmin Laferriere, San Francisco, CA (US)

(73) Assignee: Johnson & Johnson Vision Care, Inc, Jacksonville, FL (US)

( * ) Notice: Subject to any disclaimer, the term of this patent is extended or adjusted under 35 U.S.C. 154(b) by 0 days.

(21) Appl. No.: 15/222,931

(22) Filed: Jul. 28, 2016

(65) Prior Publication Data

US 2017/0127933 A1    May 11, 2017

Related U.S. Application Data

(60) Provisional application No. 62/198,656, filed on Jul. 29, 2015.

(51) Int. Cl.
*A61B 3/02* (2006.01)
*A61B 3/028* (2006.01)
*A61B 3/00* (2006.01)
*G02B 3/12* (2006.01)
*G02C 7/04* (2006.01)

(52) U.S. Cl.
CPC .......... *A61B 3/0285* (2013.01); *A61B 3/0025* (2013.01); *A61B 3/0033* (2013.01); *A61B 3/0041* (2013.01); *A61B 3/0075* (2013.01); *A61B 3/028* (2013.01); *G02B 3/12* (2013.01); *G02C 7/047* (2013.01)

(58) Field of Classification Search
CPC ......... A61B 3/0285; A61B 3/04; A61B 3/028; A61B 3/02
USPC ......................................... 351/223, 227–231
See application file for complete search history.

(56) References Cited

U.S. PATENT DOCUMENTS

| | | | |
|---|---|---|---|
| 6,619,799 | B1 | 9/2003 | Blum |
| 8,313,828 | B2 | 11/2012 | Widman et al. |
| 8,317,505 | B2 | 11/2012 | Widman et al. |

(Continued)

FOREIGN PATENT DOCUMENTS

EP    2870910 A1    5/2015

OTHER PUBLICATIONS

PCT Search Report PCT/US2016/044264 dated Oct. 7, 2016.

*Primary Examiner* — Mahidere S Sahle

(57) ABSTRACT

A system and method for assessing optical corrective needs of a patient. The system includes a computer system including a processor adapted to run at least a refractive software application thereon, an input device in communication with said processor and adapted to receive input from a user, and a displace device in communication with said processor and adapted to display information, and refractive eyewear including electrically adjustable left and right lenses selectively controllable to adjust at least a sphere power of the respective lenses and in communication with the processor. The refractive software application receives input from the input device and the eyewear controller, and selectively adjusts the sphere power of the left and right lenses, controls information displayed on said display device, and stores information regarding the sphere power of the respective left and right lenses.

5 Claims, 8 Drawing Sheets

(56) References Cited

U.S. PATENT DOCUMENTS

| | | |
|---|---|---|
| 9,645,412 B2 | 5/2017 | Wildsmith et al. |
| 2003/0174282 A1* | 9/2003 | Itagaki ................... A61B 3/04 |
| | | 351/200 |
| 2004/0263782 A1* | 12/2004 | Jones ................. A61B 3/0285 |
| | | 351/221 |
| 2009/0153796 A1 | 6/2009 | Rabner |
| 2014/0055744 A1 | 2/2014 | Wildsmith |
| 2014/0368795 A1 | 12/2014 | Liang |
| 2015/0359423 A1* | 12/2015 | Chuang ............... G02C 13/003 |
| | | 351/227 |

* cited by examiner

SYSTEM AND METHOD FOR DETERMINING CORRECTIVE VISION

CROSS-REFERENCE TO RELATED APPLICATIONS

This application claims priority to U.S. Provisional Application No. 62/198,656 (filed on Jul. 29, 2015), the contents of which are incorporated by reference in their entirety.

FIELD OF THE INVENTION

The present invention relates generally to the field of contact lenses, and more particularly to a system and method for determining corrective vision needs for patients.

BACKGROUND

The use of contact lenses to correct vision is common place in today's world. There are presently several traditional methods of high-volume low-cost contact lens manufacture. These methods include, but are not limited, to cast molding, spin casting, lathing, and using a technique known in the industry as "Lightstream Technology", and any combinations thereof.

Traditional cast molding involves the use of diamond point turning technologies to produce metal tools (also referred to as inserts) that are used in the injection molding process to produce male and female plastic lens molds. Liquid monomer is placed between the pair of male/female molds and is cured. Subsequently, the cured lens is removed from the mold pair and undergoes post processing steps (including hydration, release, sterilization, inspection, measurement, packaging, etc.) which results in a usable product.

Typically, spin casting also involves the use of diamond point turning technologies to produce metal tools that are used in the injection molding process to produce female plastic lens molds, into which liquid monomer is dosed. The mold and monomer are then spun about a central axis while being exposed to curing radiation and the lens is formed. Similar to cast molding, the cured lens is removed from the lens mold and undergoes post processing steps (including hydration, release, sterilization, inspection, measurement, packaging, etc.) which results in a usable product.

Typically, lathing involves the use of diamond point turning technologies to produce pre-hydrated lenses directly from lens blanks (also called buttons). The pre-hydrated lens then undergoes post processing steps including hydration, sterilization, inspection, measurement, packaging, etc., which results in a usable product.

Diamond point turning can also be used to produce the lens molds directly, with these lens molds being utilized in the cast molding or spin casting descriptions above.

"Lightstream Technology" is a technology used by Ciba Vision Corporation of Duluth, Ga. (now Alcon) which involves the use of re-usable glass mold pairs instead of plastic molds. Each glass mold pair consists of a concave surface mold and a convex surface mold that are submerged in lens monomer, placed close to each other so that the gap between the two curved surfaces map to the desired pre-hydrated contact lens profile. The monomer is cured through the glass molds using ultraviolet light, the molds separated and then the lens undergoes stages including hydration, sterilization, inspection, measurement, packaging, etc., which results in a usable product.

Most contact lenses produced and sold today are in discrete parameter ranges, which include limited base curves, diameters and powers. Sphere power offerings vary by manufacturer, but are usually in the range of −20.00 D to +20.00 D, more likely −12.00 D to +8.00 D. Typically, powers within these ranges are only offered in 0.25 D steps (between the range of −6.00 D and +6.00 D powers) and 0.50 D steps outside the ±6.00 D range. Currently, most cylinder power offerings are also in discrete steps, with each manufacturer having their own ranges. The Acuvue® brand of astigmatic lenses, manufactured and sold by Johnson & Johnson Vision Care of Jacksonville, Fla., for example, currently only offers −0.75 D, −1.25 D, −1.75 D and −2.25 D of cylinder correction. The available power axes of astigmatic lenses are also limited, typically in 10° steps, ranging from 0° to 180° for low cylinder powers, and restricted by some manufacturers further to say 80°, 90°, 100°, 170°, 180° and 190° (the 180° and 190° angles may be referred to as the 0° and 10° angles respectively) offerings for high cylinder powers.

The reasons for manufacturers only offering discrete steps in contact lens parameters are many, but may include the cost of tool and mold manufacture, inventory costs for storing large numbers of stock keeping units (SKUs) of the tools, inventory costs of storing huge quantities of lenses, the low prevalence of patients needing higher degrees of power correction, etc. As an example, consider the number of SKUs for a fictional astigmatic product called "BrandX" which has 1 base curve offering and 1 diameter offering. A sphere power range of −6.00 D to +6.00 D in 0.25 D steps for BrandX results in 49 different SKUs. Cylinder power offerings of say −0.75 D, −1.25 D, −1.75 D and −2.25 D along just one axis quadruples the number of SKUs to 196. Axis offerings for BrandX, say at every 10° for each of the cylinder powers, multiplies the SKUs by 18 to give 3528 SKUs. Each incremental cylinder power offering at each of the 10° axes adds 882 SKUs to BrandX's portfolio. If cylinder powers were offered in 0.25 D steps from −0.25 D to −2.25 D, the total number of BrandX SKUs would be 7938. Just one additional base curve offering doubles the SKUs to 15,876, and adding just one other diameter to the mix doubles the total again to 31,752 SKUs. Offering BrandX's axes in 5° instead of 10° increments also doubles the number of SKUs to 63,504. Offering BrandX in alternate materials also drastically increases the number of SKUs.

Offerings of different lens designs, power, base curve, diameter and shape all require different tools to be made. In a cost range of $100-$500 per metal tool, cast molding for a large number of SKUs is a very expensive proposition, especially when multi-cavity technology is used wherein multiple tools of the same design are used in each mold block. Manufacturers therefore are selective as to the number of different contact lens design options they produce, which typically are chosen to align with the most commonly prevalent vision need/ordered prescriptions. This, of course, means that individuals whose prescriptions fall between or outside those ranges offered by manufacturers must purchase lenses that are less than optimal in correcting their particular vision or fit needs.

More recently, a new system and method for manufacturing contact lenses has been disclosed in which an infinite number of different lens shapes and lens parameters (including lens powers) can be produced on a custom basis. U.S. Pat. No. 8,317,505, which is incorporated herein by reference in its entirety, discloses a method for growing a Lens Precursor Form on a single male optical mandrel on a voxel by voxel basis by selectively projecting actinic radiation through the optic mandrel and into a vat or bath of liquid polymer. The optical mandrel and Lens Precursor Form are then removed from the vat and inverted so that the convex surface of the optic mandrel is upright. Following a dwell period during which uncured residual liquid monomer from the bath that remains on the Lens Precursor Form flows under gravity over the Lens Precursor Form, such liquid is then cured to form the final lens. As described therein, a custom lens can be produced for any given eye.

The ability to manufacture highly precise and truly custom contact lenses will be truly beneficial to a patient only so far as a truly accurate, custom prescription can be generated for that patient.

The conventional method for performing an initial determination of the corrective needs for a patient leverages the well-known phoropter devices, which depend on subjective input from the patient to advise the eye care practitioner as to which of various lenses placed before his or her eye provides better corrected vision. Phoropters, however, typically have discrete, stepped resolutions for focus error and cylindrical error, usually 0.125 and 0.25 diopters respectively, although some newer devices can achieve higher resolutions of 0.01 diopters. Zeroing in on an accurate corrective need for a patient using a phoropter is a time consuming process, with at each step the practitioner having to use judgment to select the next proposed lens and manually do so, and the patient having to compare one selection to the other and provide feedback to the practitioner. With three independent variables, focus error, cylindrical power and cylindrical axis, time constraints may limit the accuracy of the end result. Human error, both that of the patient and the practitioner, are necessarily present. Further, subjective determination of cylindrical axis is difficult because slight differences can have a large impact on cylindrical correction. Further, as indicated, the accuracy of a determined corrective need is limited by the resolution of the phoropter used. Phoropters can determine sphere, cylinder and axis, but not higher order aberrations.

Objective measurement devices and techniques have also been used to measure a patient's eye and subsequently determine corrective needs for that patient. These devices, known as refractometers and aberrometers, typically display sphere power data to the nearest one hundredth of a diopter, and the nearest whole integer for axis in degrees. Exams performed using refractometers and aberrometers are typically referred to as "objective exams" since the equipment returns numerical and graphical values with little to no patient involvement in the decision making process. One example of an auto-refractometer is the Nidek ARK-10000 Refractive Power/Corneal Analyzer (Nidek Inc. of Freemont, Calif.). The 0.01 D power resolution and 1° axis resolution of refractometers and aberrometers suggests that they would be ideal for use in the process of prescribing custom lenses. Objective exams, however, do not take into account how the brain perceives and analyzes the images presented to it by the ocular system and, therefore, do not always provide the best prescriptive data for all patients. When fitted with lenses prescribed via the use of subjective data compared to lenses prescribed based on objective data, some patients prefer the "subjective lenses" and others prefer the "objective lenses." This being said, the sphere, cylinder and axis data from objective exams can be used alone, or in combination with data from subjective exams to provide the best possible custom lens design for the patient.

Some attempts have been made to combine subjective feedback obtained using a phoropter with objective data such as that obtained from an aberrometer. One such example is described in U.S. Patent Publication No. 2014/0368795. Although this method does describe leveraging a combination of objective and subjective data, it is still plagued by the disadvantages of the phoropter described above, most notably the time consuming process, involvement of the practitioner in the process, and patient difficulty in choosing at each steps which of two options is better when lenses are flipped back and forth before them.

SUMMARY OF THE INVENTION

A system is provided for assessing optical corrective needs of a patient, including a computer system having a processor adapted to run at least a refractive software application thereon, an input device in communication with the processor and adapted to receive input from a user, and a displace device in communication with the processor and adapted to display information. The system further includes refractive eyewear adapted to be worn by a patient and that includes electrically adjustable left and right lenses each adapted to be selectively controllable to adjust at least a sphere power of the respective lenses. The refractive eyewear is in communication with the processor; and an eyewear controller having at least first and second input devices in communication with the processor. The first and second input devices are adapted to selectively adjust the sphere power of the respective left and right lenses. The refractive software application is adapted to receive input via the input device, receive input via the eyewear controller, selectively adjust the sphere power of the electrically adjustable left and right lenses based on input from the input device and/or eyewear controller, control information displayed on the display device, and store information regarding the sphere power of the respective left and right lenses.

In one embodiment, refractive eyewear and eyewear controller are wirelessly coupled to the computer system for communication therebetween.

In yet another embodiment, the refractive software application is further adapted to receive cylinder and axis input data for the patient via the input device, and to produce as output the sphere power of the left and right lenses as adjusted by the patient via the eyewear controller, and the cylinder and axis data. The refractive software application may further be adapted to generate a design for a custom contact lens based on the outputted sphere power and cylinder and axis data.

The refractive eyewear may further include a plurality of clips adapted to engage and hold in place first and second spectacle lenses in a position so as to overlay the first and second electrically adjustable lenses respectively.

In yet another embodiment, the electrically adjustable left and right lenses are variable optic liquid lenses, and the sphere power of the left and right lenses are adjusted by varying an electric field applied across the respective liquid lens.

The refractive eyewear may further include an interpupillary adjustment device, and may also include an interpupillary adjustment scale. The refractive eyewear may also further include a nose bridge height adjustment device.

In yet another embodiment, the refractive eyewear further includes left and right earpieces, and a left and right earpiece distance adjustment device for adjusting a length of the left and right earpieces respectively, and may also include a left and right earpiece angle adjustment device.

A method is also provided for assessing optical correction needs of a patient including fitting refractive eyewear to a patient's head, which includes electrically adjustable left and right lenses adapted to be selectively controllable to adjust at least a sphere power of the respective lenses;

providing an eyewear controller to the patient that has at least first and second input devices adapted to selectively control the sphere power of the respective left and right lenses; displaying a blurred image to the patient on a display device while the patient is wearing the refractive eyewear; allowing the patient to adjust the sphere power of the left and right lenses using the left and right input devices respectively until the image is no longer blurred to the patient; recording the sphere power of the adjustable lenses following completion of adjustment by the patient; selecting fitting lenses for the patient's left and right eyes having a sphere power that most closely matches the recorded sphere power for each eye; performing an objective examination on the patient while the patient is wearing the fitting lenses to obtain cylinder and axis error data for said patient for each eye; replacing the refractive eyewear on the patient's head; displaying a blurred image to the patient on a display device while the patient is wearing the refractive eyewear and selected fitting lenses; allowing the patient to adjust the sphere power of the left and right lenses using the left and right input devices respectively until the image is no longer blurred; recording the sphere power of the adjustable lenses following completion of the second adjusting step; and conveying the sphere power from the second recording step, and the cylinder and axis error data for the purpose of generating a design for a custom contact lens for the patient.

In one embodiment, the method further includes fitting a patient with refractive eyewear including electrically adjustable left and right lenses adapted to be selectively controllable to adjust at least a sphere power of the respective lenses; providing the patient with an eyewear controller having first and second input devices adapted to selectively adjust the sphere power of the respective left and right lenses; initiating refraction application software to be used in evaluating the patient, the refraction application software being resident on a processor in a computer system the computer system further including an input device in communication with the processor and adapted to receive input from a user, and a displace device in communication with the processor and adapted to display information, the initiating step further including establishing communication as between the refraction application software and the refractive eyewear and the eyewear controller; performing a base spherical eye refraction on the patient by presenting a blurred image to the patient on the display device, and allowing the patient to adjust the sphere power of the left and right lenses using the left and right input devices on the eyewear controller until the image is no longer blurred; selecting fitting lenses for the patient that most closely match the adjusted sphere powers of the refractive eyewear; instructing the patient to wear the selected fitting lenses; performing an objective examination while the patient is wearing the fitting lenses to obtain cylinder and axis error data for the patient; and performing a second spherical eye refraction on the patient while the patient is wearing the fitting lenses by presenting a blurred image to the patient on the display device, and allowing the patient to adjust the sphere power of the left and right lenses using the left and right input devices on the eyewear controller until the image is no longer blurred.

In yet another embodiment, the method further includes obtaining the sphere power of the right and left lenses of the refractive eyewear following the second spherical eye refraction step, and utilizing the sphere powers, and the obtained cylinder and axis data, to prescribe a custom contact lens for the patient.

In another embodiment, the method further includes selecting a fiducial fitting lens including fiducial indicators, performing an objective examination while the patient is wearing the fiducial fitting lens using a measuring device including an optical imaging device, obtaining optical images of the fiducial fitting lens on the patient's eye using the optical imaging device, determining decentration and/or rotation information of the fiducial fitting lens from the optical images, and utilizing the decentration and/or rotation information in conjunction with the sphere powers and the obtained cylinder and axis data to prescribe a custom lens for said patient.

The fitting lens and the fiducial fitting lens may alternatively be the same lens or different lenses. Further, the fiducial indicators may be fiducial marks or lens edge features.

These and other objects, features and advantages of the present invention will be apparent from the following detailed description of illustrative embodiments thereof, which is to be read in connection with the accompanying drawings.

DETAILED DESCRIPTION

Figure 1:
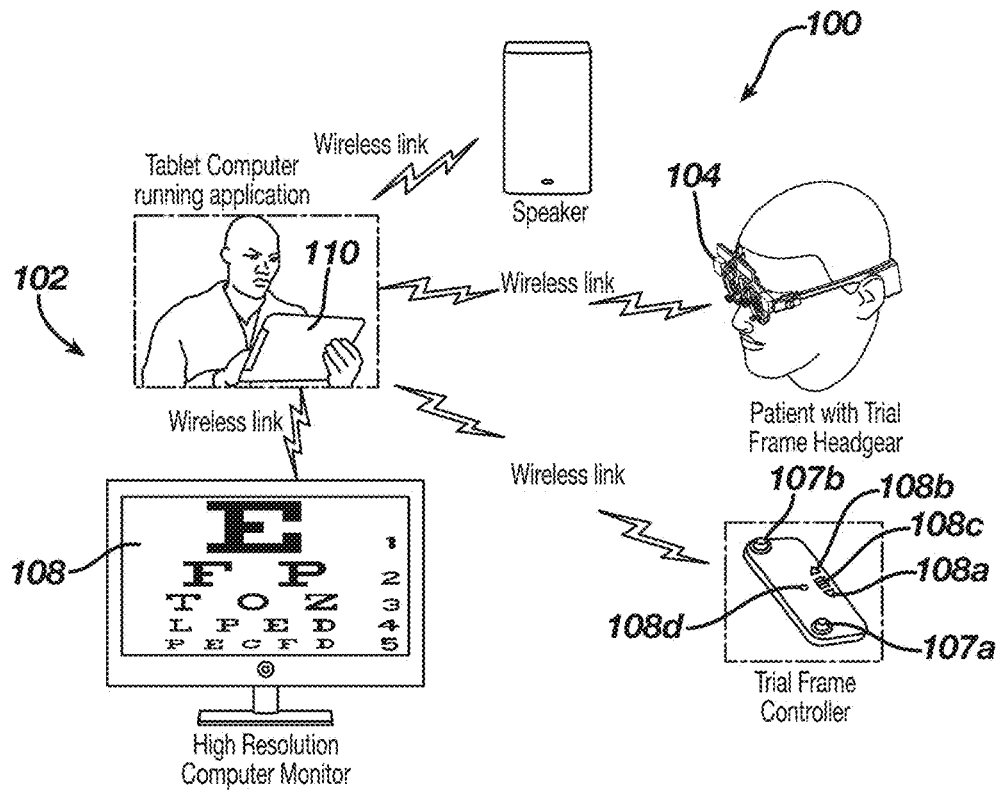
FIG. 1 illustrates an exemplary system for measuring optical needs of a patient.

Referring now to FIG. 1, a preferred embodiment of a system for assessing optical corrective needs of a patient 100 includes a computer system 102 including computer 110 such as a tablet, laptop or desktop having a refraction software application loaded thereon, a high resolution display 108 such as a computer monitor, refractive eyewear 104 to be worn by the patient, and an eyewear controller 106 that adjusts at least sphere power in the refractive eyewear 104 lenses. In the illustrated embodiment, the computer 110 is wirelessly connected to the display device 108, and runs the refractive software application that controls the display presented to the patient. The computer 110 is further wirelessly connected, such as by a Bluetooth Low Energy communication link, to the refractive eyewear 104, and similarly to the eyewear controller 106. Although the described embodiment is preferred, those skilled in the art will readily understand that any suitable computer system can be implemented that is capable of running the application software and displaying images and information to the patient and practitioner as described further below, and that any suitable connection means, wireless or not, can also be implemented.

The refractive software application displays various images on the display device 108, accepts input from the patient via the eyewear controller 106, and controls the refractive eyewear according to this input, and also can receive input from the practitioner via the tablet device 110 to control the display and refractive eyewear. The refractive software application can also provide various audio or visual prompts to the patient to give instructions or help.

The eyewear controller 106 preferably includes first and second input devices such as rotary adjustment knobs 107a, 107b to adjust the left and right lenses of the refraction eyewear 104 respectively, and three input buttons. The buttons are preferably assigned so that pressing one 108a enables the user to go back one step in the procedure as established by the refractive software application, pressing the second 108b enables the user to go forward one step in the procedure, and pressing the third 108c allows the user to solicit help with the process.

The refractive eyewear 104 is shown in greater details in FIGS. 2 and 2a-2e. The eyewear 104 is similar in appearance to an oversized set of eyeglasses, and includes a right lens 120 and a left lens 122 that are variable optic lenses and selectively adjustable to enable refractive spherical correction preferably between +/−10 diopters and preferable in 0.02 to 0.03 diopter increments. Variable optic lenses are known in the art, with one type enabling adjustable refractive correction by applying an electric field across a "liquid" lens. The magnitude of correction is roughly proportional to the magnitude of the electric field applied across the lens, and can accommodate a resolution of 0.02 to 0.03 diopters, which is far greater than the human eye/brain can detect. One exemplary suitable variable optic lens that can be used is Artic 39N0, which is manufactured and sold Varioptic, Inc. of Lyon, France. Additional models with a larger aperture are also available. As indicated, the eyewear controller includes two rotary adjustment knobs that communication through the application software to apply the requested electric field/correction to the respective lenses in the eyewear, and the application software tracks the applied correction.

Figure 2:
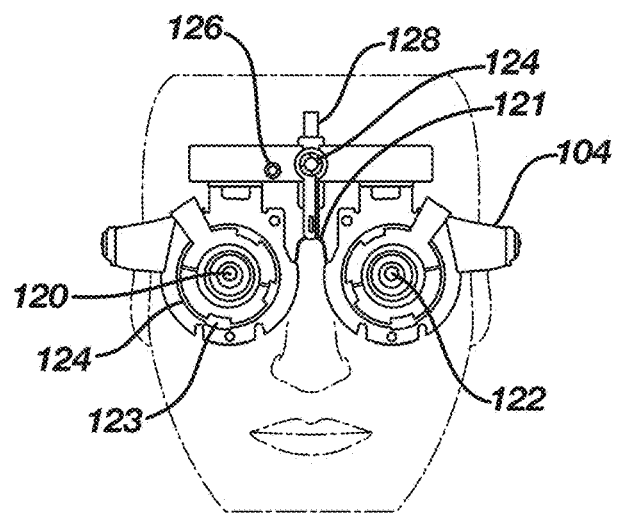
FIG. 2 is a front view illustrating exemplary refractive eyewear fitted to a patient.
Figure 2A:
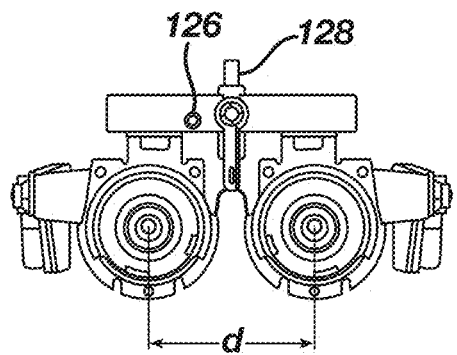
FIG. 2a is a front view of the refractive eyewear of FIG. 2.
Figure 2B:
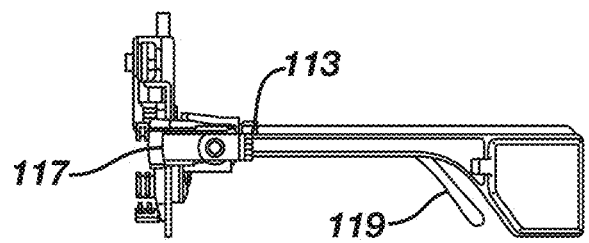
FIGS. 2b and 2c are side and perspective views of the refractive eyewear of FIG. 2.
Figure 2C:
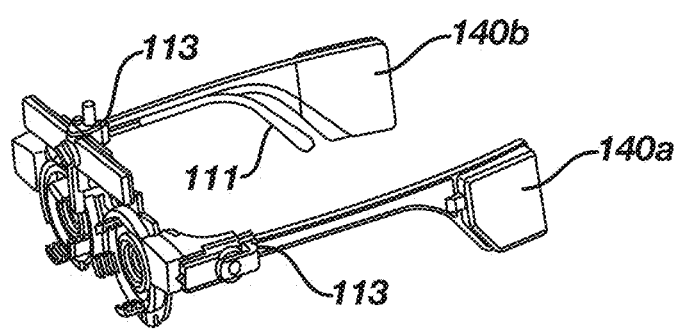

The refractive eyewear further includes a number of mechanical adjustment mechanisms to fit the device to the unique size and shape of a particular patient's head. Referring to FIG. 2a, an inter-pupillary distance (distance between pupils) adjustment device 124, preferably a rotatable knob, allows adjustment of the inter-pupillary distance "d" to better fit the patient, and preferably spans a range from at least 54-70 mm. The eyewear further includes an inter-pupillary distance scale 126 indicating the set distance. The nose bridge height of the refractive eyewear can also be adjusted using the nose bridge height adjustment mechanism 128, preferably a rotatable knob that raises or lowers the nose bridge height.

The left (not shown) and right earpieces 111 (FIGS. 2b and 2c) can also be adjusted. An earpiece angle adjustment device 113 on each side allows the respective earpieces to be selectively adjusted up to about 5 degrees up or down from horizontal, with the angular adjustment indicated by angular adjustment gauge 117. Also, the distance to the natural curve of the bow 119 can be adjusted up to approximately 30 mm by sliding the earpiece 111 forward or backward via the distance adjustment devices 114. The left and right earpieces 111 are adjusted independently of the position of the controllers 140a, 140b, which are described further below.

Referring back to FIG. 2, the refractive eyewear is designed to also accommodate optional standard fixed lenses, which may be used to account for cylinder and axis error during the examination as described further below. The fixed lenses can be held in place by clips 123. Further, an angular scale 124 about the perimeter can be used to adjust the axis of the standard fixed lens as will also be described further below.

Figure 2D:
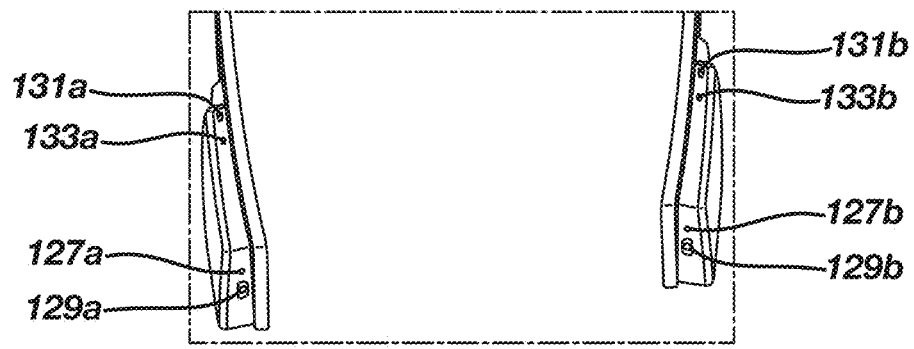
FIG. 2d is a perspective view of controllers on the refractive eyewear of FIG. 2.

Various other features of the refractive eyewear can be best seen in FIG. 2d, which illustrates the left and right wireless lens controllers 140a, 140b that communicate with the refractive software application to control spherical refraction of the electrically adjustable lenses 120, 122. Charge indicator lights (i.e., LEDs) 127a, 127b and charge ports 129a, 129b, such as a USB battery charge port, are present on both the left and right controllers. The eyewear also preferably includes status indicators 131a, 131b and wake up buttons 133a, 133b on each side.

As indicated previously, the eyewear controller 106 includes first and second rotatable knobs 107a, 107b that includes features that enable the user to manually control spherical refractive changes to the left and right adjustable lenses 120, 122 in the refractive eyewear respectively. The knobs may optionally be dual function where pressing of the respective knobs causes forward or backward navigation respectively through the procedure, or could include separate buttons 108a, 108b for these navigation features as described previously. An additional button 108c functions as a "help" button when the user requires assistance with the procedure, and can also function as a wake-up button where the controller has gone into sleep mode.

System Setup and Procedure

Figure 3:
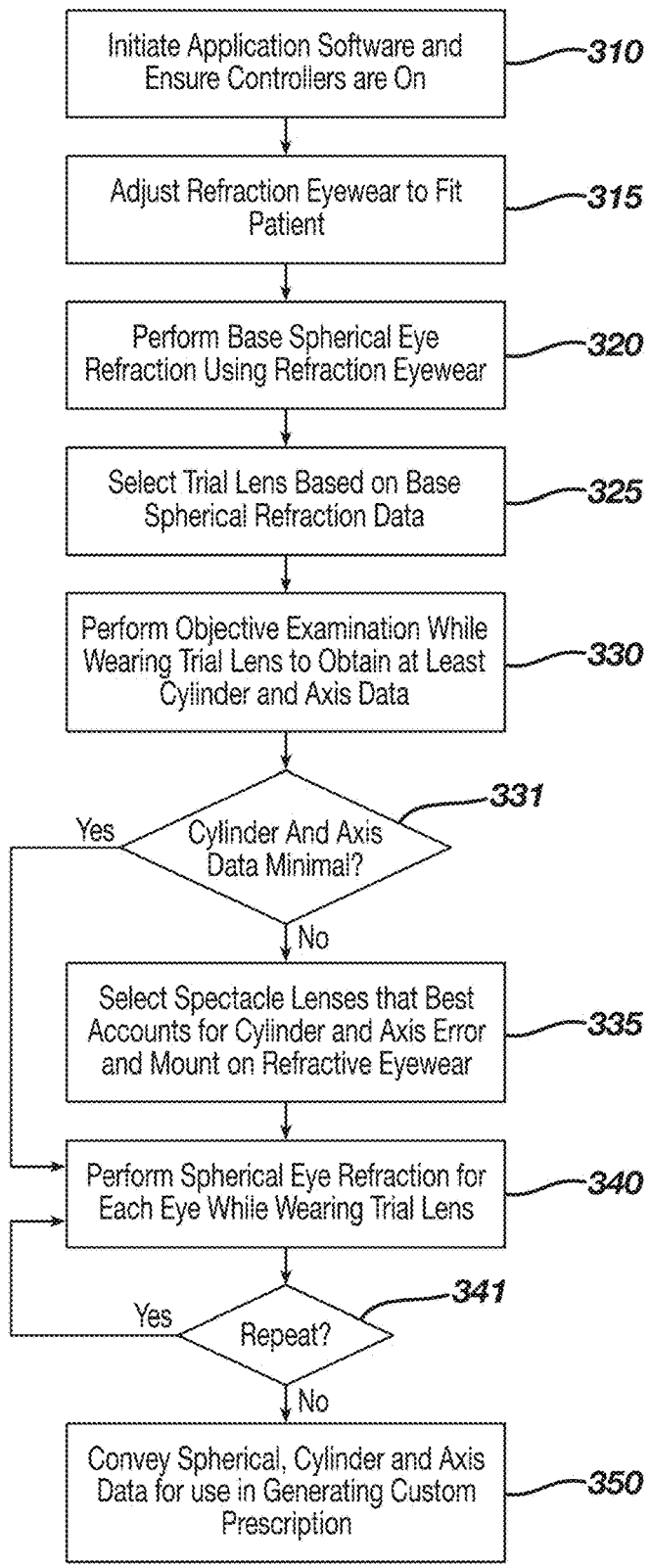
FIG. 3 illustrates an exemplary method for determining optical corrective needs for a patient.

Referring now to FIG. 3, the system setup and procedure will now be described in detail. The practitioner begins by initiating the refractive software application 310 application on the tablet or personal computer device. Initiation of the application should turn on both controllers on the respective earpieces of the refractive eyewear and the eyewear controller, which will cause the status indicator LEDs 131a, 131b, 108d on these devices to turn green. If the LED on the controller is not green, pushing the "help" button 108c on the controller will manually turn on the controller. If the LEDs on the controllers of the refractive eyewear are not green, then the practitioner can similarly push the wakeup buttons 133a, 133b to manually turn them on. The LEDs preferably are designed to remain on steadily when actively connected to the application, to flash approximately every five seconds when in standby mode, and to indicate a dead battery when not lit at all. Further, the LED may also incorporate different colors, for example, with yellow indicating that less than 25% battery life remains, and red indicating that less than 5% battery life remains.

As part of its initiation process, the software application will establish the wireless connection with eyewear controller and the left lens controller 140a and right lens controller 140b. Once communication with these devices has been established which can take several seconds, the application will indicate that it is ready for operation with a steady green light.

Following system set up, the eye care practitioner will properly fit the refractive eyewear to the patient 315. Before being placed on the patient, a preliminary adjustment is made by extending the left and right earpieces to their furthest possible extension using the earpiece distance adjustment devices 114, adjusting the nose bridge 121 to its highest point by manipulating rotatable knob 128, and setting an initial estimate of the inter-pupillary distance.

Figure 2E:
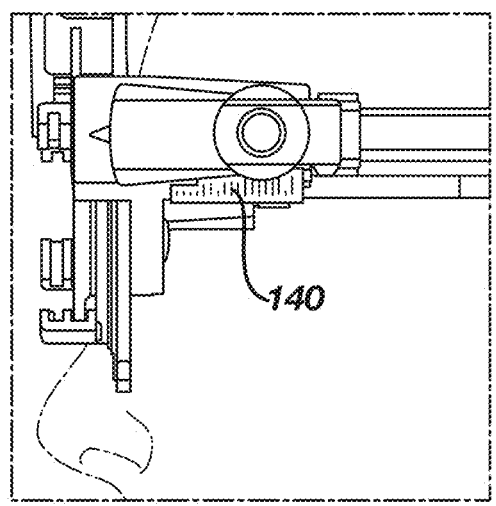
FIG. 2e is a side view of an adjustment mechanism on the refractive eyewear of FIG. 2.

The refractive eyewear is then placed on the patient and slid back until the distance between the eyewear lens and the patient's pupil is 12.3 mm, which is indicated as zero on the side scale 140 (see FIG. 2e). If alignment at the zero point is not possible, the practitioner records the actual distance from the side scale, with each tick mark on the side scale representing a 1 mm deviation. Next, the left and right earpieces are fitted by sliding them forward until the ears are captured and the headgear rests on the head without sliding down the nose. The patient is then instructed to view the display 108 to verify that the plane of the lenses (or plane of the front of the refractive eyewear) is roughly parallel to the plane of the display. If needed, the earpiece angle adjustment device 113 can be used to adjust the plane of the lenses to as close to parallel as possible. The nose bridge height is then adjusted so that the center of the patient's pupils is vertically aligned with the center of the refractive eyewear lenses. The inter-pupillary distance can then be fine-tuned so that the centers of the pupils are horizontally aligned with the center of the refractive eyewear lenses.

Once the refractive eyewear is properly fitted to the patient, the patient is given the eyewear controller and instructed on its operation, and the evaluation procedure is ready to begin. An initial, gross or base spherical eye refraction is performed first 320, with the practitioner first adjusting the electrically adjustable lenses 120, 122 via tablet 110 until the display is entirely blurred for the patient. The patient then adjusts the left and right knobs 107a, 107b of the eyewear controller 106, one at a time, until the image on the display comes into focus, and the respective spherical data from the refractive eyewear is recorded by the refraction software application.

Once the baseline spherical refraction is established, the practitioner then will select at step 325 available "trial" or "fitting" contact lenses that most closely matches the spherical values obtained in step 320. Next, while wearing the fitting lenses, cylindrical and axis values for the patient are obtained 330 by any suitable means. As described earlier, cylinder is difficult to accurately determine using subjective means (i.e., phoropter) since slight differences can have a large impact on cylinder. Thus, in a preferred embodiment, objective cylinder and axis measurements are obtained using a wavefront aberrometer, such as the OPD Scan III which is manufactured and sold by Nidek, Inc. of Freemont, Calif.

The cylinder and axis error data is input into the refractive software application by the practitioner. The practitioner then selects available spectacle lenses that most closely will correct the cylinder and axis error, and places them within the clips 123 on the refractive eyewear, using the angular scale 124 to best approximate the axis error.

If such trial or spectacle lenses are not available, or if the errors are minimal, the practitioner will proceed directly to step 340 where the patient again uses the refractive eyewear to determine a more precise spherical refraction for each eye while the patient continues to wear the fitting lenses. Beginning with, for example, the left eye, the practitioner would adjust the electrically adjustable right lens 122 via the software application so that it is completely blurred for the patient, and then adjust the lens 120 for the left eye so that is slightly blurred, such as approximately 2 diopters from the baseline spherical measurement determined above. The patient then adjusts the knob 107a until the image is best brought into focus for the left eye. The spherical refraction for the other eye is then determined in the same manner. These two steps (measuring left and/or right eye) can optionally be repeated (step 341) 2-3, or more, more times until the refraction numbers are being consistently repeated.

At this point the practitioner has obtained cylindrical and axis data from the objective examination, and very precise spherical values using the refractive eyewear initially, and then as further applied over a selected fitting lenses.

The axis, spherical and cylindrical data can now be used to generate a custom prescription for that patient 350. Preferably, the custom lens will be a Free Form custom lens manufactured as described in detail in, for example, U.S. Pat. No. 8,313,828, which is incorporated herein by reference in its entirety. More preferably, the fitting lenses will also be a Free Form lens, and the ultimate custom lens prescription will be determined using the resulting spherical, cylindrical and axis data in the manner set forth in co-pending U.S. patent application Ser. No. 14/534,106, filed on Nov. 5, 2014 and entitled "Customized Lens Device and Method," which is incorporated herein by reference in its entirety.

In an alternate embodiment, the practitioner may collect additional data that can be used to generate a custom contact lens prescription for the patient, such as translation and rotational error data representing how the fitting lens actually behaves on the patient's eye. The existence and extent of translational and rotational error for any given contact lens is unique to a specific patient due to the unique physical properties of that patient's eye and surrounding structures such as eyelids. If how a particular lens behaves when on the eye can be measured, the information can be used to better design a subsequent lens that will account for this behavior and further optimize optical correction.

It is well known that a slit lamp in combination with a fitting lens having fiducial marks can be used to assess the location or movement of the lens on the patient's eye. A slit lamp is typically described as a low powered microscope combined with a high-intensity light source that can be focused into a thin beam. Some slit lamps may provide a magnified three-dimensional view of different parts of the eye. A camera may be used to capture these different images. Using the slit lamp, the eye care practitioner gauges the position error of the lens by referencing the fiducial marks via the light beam from the slit lamp. The physical distortion of the light beam and the angle at which the beam is directed at the lens allows an eye care practitioner, using experience and judgment, to view the position error and decide if another lens should be selected for the patient that would better account for the position error seen with the initial lens.

Some lenses may be configured to have edge features that can be used in conjunction with a slit lamp to assess fitting of the lens on the eye rather than fiducial marks on the lens. For example, lens configurations such as those described in U.S. Patent Publication No. 2014/0055744, which is incorporated herein by reference in its entirety, disclose such lens designs. Visualization of a lens edge feature during examination with a slit lamp can be enhanced with fluorescein to illuminate the lens relative to the patient's eye.

As mentioned above, however, precision corrections require precision measurements. Due to the slit lamp method where visual judgment is used by the eye care practitioner, the precision in position error detection may be lacking for a true precision lens. To overcome this, an objective wavefront measurement may be used to provide better precision over a slit lamp for viewing fiducial marks to determine position error.

In this regard and with reference now to FIGS. 4 and 5a-5e, digital images of the trial lens having fiducial marks or edge features are taken using an optical imaging device.

Figure 4:
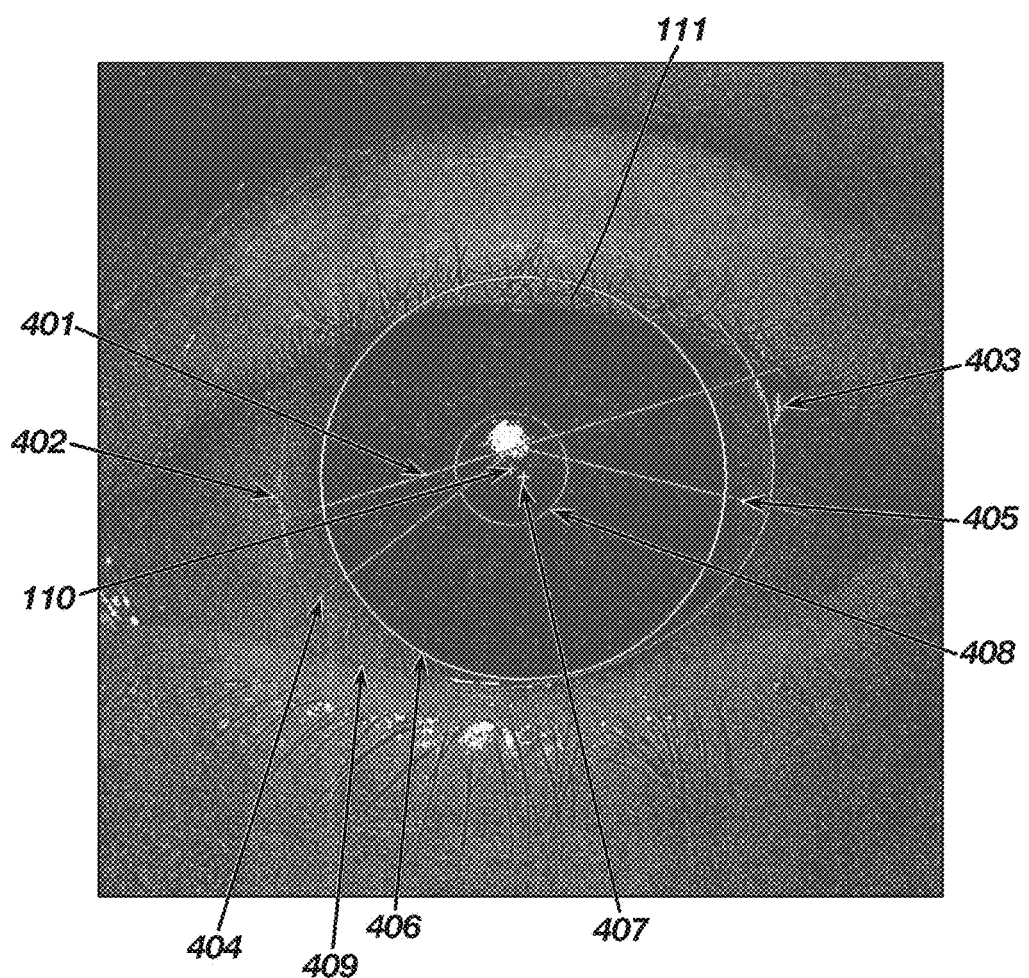
FIG. 4 illustrates a digital image of a patient's eye while wearing a contact lens.
Figure 6:
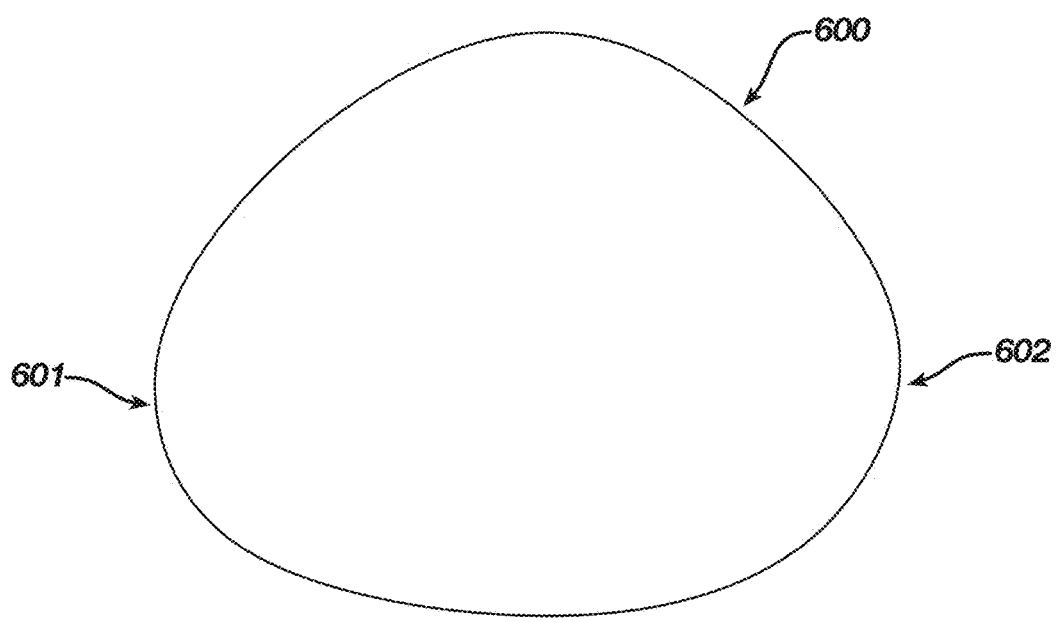
FIG. 6 illustrates an exemplary lens having lens lobes as shown apart from a patient's eye.

Referring now to FIG. 4, the digital image is overlaid with reference points from which the imaging device extracts imaging data. At 401, a lens rotation axis represents the rotation of the lens as it orients itself on the patient's eye. A lens with no rotation would have a lens rotation axis of zero degrees. Reference numerals 402 and 403 represent 1 degree index points both clockwise and counterclockwise relative to the lens rotation axis. These index points may also be in the shape of a protruding portion of the lens edge, such as the exemplary lens "lobes" which serve as lens alignment indication axes for geographical feedback. These lens "lobes" are illustrated by reference numeral 404 and 405 in FIG. 4, and as 601 and 602 in the exemplary lens 600 of FIG. 6 illustrated apart from the eye. Reference numeral 406 represents the limbal boundary of the eye, 407 represents the limbal center of the eye, 408 the pupil boundary of the eye, and 409 the lens boundary as the lens sits on the eye.

Figure 5A:
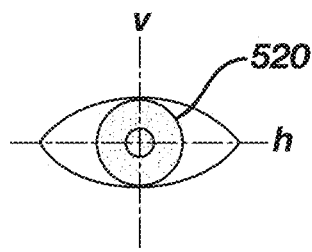
FIGS. 5a-5d are various illustrations of a patient's eye with and without a contact lens overlay.
Figure 5B:
Figure 5C:
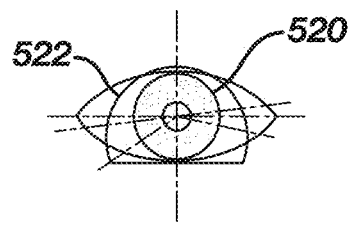
Figure 5D:
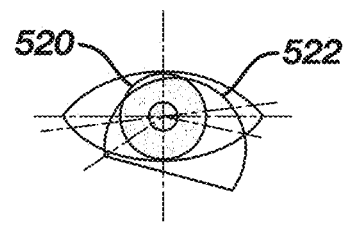

Referring now to FIGS. 5a-5e, FIG. 5a illustrates a representative image of a patient's eye 520 with a vertical (v) and horizontal (h) axis reference. FIG. 5b illustrates a representative image of a fitting lens 522, which in this exemplary embodiment is depicted as a non-round lens. FIG. 5c illustrates a representation of the contact lens 522 overlaid over the image of the eye 520 with an ideal fit having no decentration or rotational errors. FIG. 5d is an exemplary representation of a lens-on-eye system where the fitting lens 522 experiences both decentration and rotational errors when actually placed on the patient's eye 520.

Figure 5E:
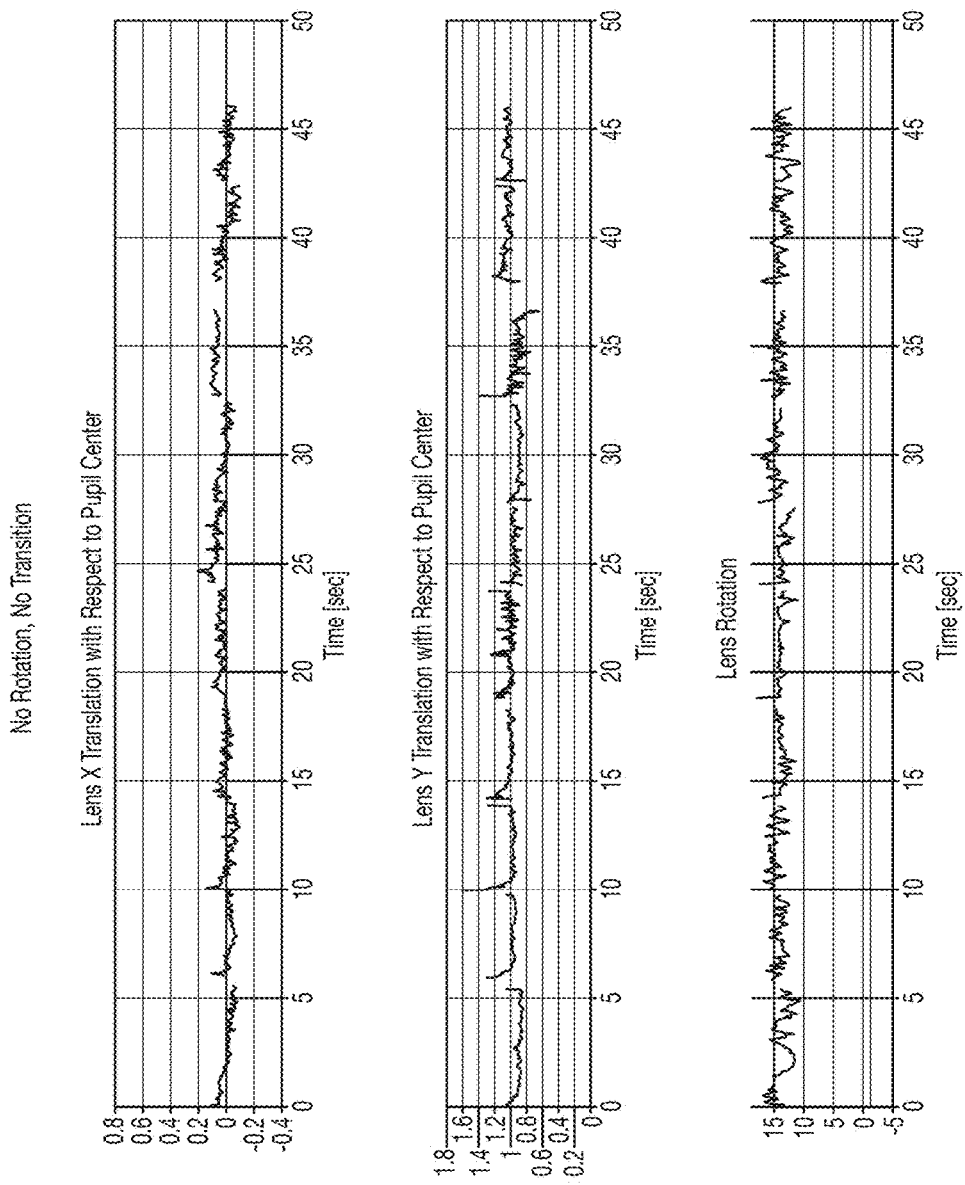
FIG. 5e illustrates data charts representing digital images of a lens-on-eye over time.

FIG. 5e illustrates a data chart derived from the digital imaging data retrieved from the optical imaging device. In this exemplary embodiment, the data is illustrated in the form of both lens rotation and decentration (translation) such as that shown in FIG. 5d. Further, the digital imaging data is plotted as a function of time. Reference numeral 506 illustrates a point in time along the rotation chart representing a moment in time when the lens rotated either clockwise or counterclockwise. Line 507 represents the decentration of the lens along the Y axis, plotted as a function of time, and line 508 represents the decentration of the lens along the X axis also plotted as a function of time.

With resulting decentration and rotational error data, the optic zone can be repositioned within the lens to better account for the errors.

Although the system and method has been described herein in conjunction with contact lens prescriptions, those skilled in the art will readily understand that the system and method can be applied to spectacle lens prescriptions as well.

Further, although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A method for assessing optical correction needs for a patient, comprising: fitting a patient with refractive eyewear including electrically adjustable left and right lenses configured to be selectively controllable to adjust at least a sphere power of the respective lenses; providing said patient with an eyewear controller having first and second input devices configured to selectively adjust the sphere power of the respective left and right lenses; initiating refraction application software to be used in evaluating said patient, said refraction application software being resident on a processor in a computer system, said computer system further including an input device in communication with said processor and configured to receive input from a user, and a display device in communication with said processor and configured to display information, said initiating step further including establishing communication as between said refraction application software and said refractive eyewear and said eyewear controller; performing a base spherical eye refraction on said patient by presenting a blurred image to said patient on said display device, and allowing said patient to adjust the sphere power of the left and right lenses using the left and right input devices on the eyewear controller until the image is no longer blurred; selecting fitting contact lenses for said patient that most closely match the adjusted sphere powers of said refractive eyewear; instructing said patient to wear said selected fitting contact lenses; performing an objective examination while said patient is wearing said fitting contact lenses to obtain cylinder and axis error data for said patient; performing a second spherical eye refraction on said patient while said patient is wearing said fitting contact lenses by presenting a blurred image to said patient on said display device, and allowing said patient to adjust the sphere power of the left and right lenses using the left and right input devices on the eyewear controller until the image is no longer blurred; obtaining the sphere and power of the right and left lenses of the refractive eyewear following the second spherical eye refraction step; and utilizing said sphere powers of said first and second spherical refractions and said obtained cylinder and axis data to prescribe a custom contact lens for said patient.

2. The method according to claim 1, further comprising:
   selecting a fiducial fitting contact lens including fiducial indicators;
   performing an objective examination while said patient is wearing said fiducial fitting contact lens using a measuring device including an optical imaging device;
   obtaining optical images of said fiducial fitting contact lens on said patient's eye using said optical imaging device;
   determining decentration and/or rotation information of said fiducial fitting contact lens from said optical images; and
   utilizing said decentration and/or rotation information in conjunction with said sphere powers and said obtained cylinder and axis data to prescribe a custom contact lens for said patient.

3. The method according to claim 1, wherein said fitting contact lens and said fiducial fitting contact lens are the same lens.

4. The method according to claim 1, wherein said fitting contact lens and said fiducial fitting contact lens are different lenses.

5. The method according to claim 1, wherein said fiducial indicators are fiducial marks or lens edge features.

* * * * *